United States Patent
Zou et al.

(10) Patent No.: US 8,194,961 B2
(45) Date of Patent: Jun. 5, 2012

(54) METHOD, APPARATUS, AND COMPUTER-READABLE MEDIUM FOR PRE-RECONSTRUCTION DECOMPOSITION AND CALIBRATION IN DUAL ENERGY COMPUTED TOMOGRAPHY

(75) Inventors: Yu Zou, Naperville, IL (US); Michael D. Silver, Northbrook, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 982 days.

(21) Appl. No.: 12/106,907

(22) Filed: Apr. 21, 2008

(65) Prior Publication Data
US 2009/0262997 A1 Oct. 22, 2009

(51) Int. Cl.
*A61B 6/03* (2006.01)
(52) U.S. Cl. ............................................ 382/131; 378/5
(58) Field of Classification Search ..................... 378/5; 382/128–132
See application file for complete search history.

(56) References Cited

OTHER PUBLICATIONS

Remeysen et al., Beam hardening artifact reduction in microfocus computed tomography for improved quantitative coal characterization, Available on line Dec. 15, 2005, International Journal of Coal Geology, vol. 67, pp. 101-111.*
Kleinschmidt, Analytical considerations of beam hardening in medical accelerator photon spectra, 1999, Medical Physics, vol. 26, No. 9, pp. 1995-1999.*
Alles et al., Beam Hardening: Analytical considerations of the effective attenuation coefficient of x-ray tomography, Jul. 2007, Medical Physics, vol. 34, No. 7, pp. 2882-2889.*
Ruth et al., A comparison of beam-hardening artifacts in x-ray computerized tomography with gadolinium and iodine contrast agents, 1995, Medical Physics, vol. 22, No. 12, pp. 1977-1982.*
Yu Zou et al., "Analysis of Fast kV-switching in Dual Energy CT using a Pre-reconstruction Decomposition Technique", Proceedings of SPIE, vol. 6913, pp. 691313-1-691313-12, Feb. 18, 2008.
European Search Report issued Feb. 23, 2012 to European Patent Application 09005600.3-2218.

* cited by examiner

*Primary Examiner* — Edward Glick
*Assistant Examiner* — John Corbett
(74) *Attorney, Agent, or Firm* — Oblon, Spivak, McClelland, Maier & Neustadt, L.L.P.

(57) ABSTRACT

A method of obtaining a computed tomography image of an object includes determining linear terms and non-linear beam hardening terms in a pair of line integral equations for dual-energy projection data from inserting average and difference from average attenuation terms, obtaining an initial solution of the line integral equation by setting the non-linear beam hardening terms to zero, and iteratively solving the line integral equations to obtain one line integral equations for each basis material. Attenuation by the first basis material corresponds to a photoelectric attenuation process, and attenuation by the second basis material corresponds to a Compton attenuation process. The line integral equations can be inverted by an inverse Radon procedure such as filtered back-projection to give images of each basis material. The images of each basis material can then be optionally combined to give monochromatic images, density and effective atomic number images, or photoelectric and Compton processes images.

15 Claims, 12 Drawing Sheets

METHOD, APPARATUS, AND COMPUTER-READABLE MEDIUM FOR PRE-RECONSTRUCTION DECOMPOSITION AND CALIBRATION IN DUAL ENERGY COMPUTED TOMOGRAPHY

BACKGROUND OF THE INVENTION

1. Field of the Invention

The present invention generally relates to the field of computed tomography imaging, and in particular, to a method, apparatus, and computer-readable medium for pre-reconstruction decompositions in dual energy computed tomography.

2. Discussion of the Background

The mathematics used in CT-reconstruction were first elucidated by Johann Radon in 1917. Once you can reduce the measured transmitted measurements to line integrals (also called the Radon transform), Radon showed how to invert the integrals (i.e., using the inverse Radon transform) to uniquely determine the integrand: a function the describes properties of interest; in this case, the linear attenuation coefficients of the various tissues in the patient.

An exact solution requires monochromatic radiation. However, all practical sources of X rays at present are polychromatic. Using an inverse Radon transform method such as filtered backprojection, may result in strong artifacts in the reconstructed image known as beam hardening artifacts (beam hardening, because as the polychromatic beam transverses the patient, the softer—lower energy—photons are preferentially absorbed or scattered out of the beam, leaving the harder photons). It is worth noting that the Radon transform and it inverse are linear equations. The beam hardening makes them nonlinear and not exactly solvable.

A possible solution to this problem is to perform a dual energy scan (i.e., scan the same object with two polychromatic scans but one at a higher energy than the other). A dual-energy computed tomography (CT) technique may generate images having reduced beam hardening artifacts and may provide some information regarding the composition of the object being imaged, for example as discussed in Alvarez, R. and A, Macovski., "Energy-selective reconstruction in x-ray computerized tomography", *Phys. Med. Biol.*, 21, 733-744, 1976, which is incorporated herein by reference in its entirety. Dual-energy CT has been applied to bone mineral to bone mineral quantification (e.g., as discussed in D. D. Faul, J. L. Cauch, C. E. Cann, A. Laval-Jeantet, D. P. Boyd, and H. K. Genant, "Composition-selective reconstruction using dual energy CT for bone mineral quantification", *J. Comput. Assist. Tomography,* 6, 202-204, 1982, which is incorporated herein by reference in its entirety), attenuation correction in nuclear medicine (e.g., as discussed in H. Hasegawa, T. F. Lang, K. J. Brown, E. L. Gingold, S. M. Reilly, S. C. Blankespoor, S. C. Liew, B. M. W. Tsui, and C. Ramanathan, "Object-specific attenuation correction of SPEC with correlated dual-energy X-ray CT", *IEEE Trans. Nucl. Sci.,* 40, 1212-52, 1993, which is incorporated herein by reference in its entirety), bone subtraction, and contrast enhancement between lesion or fatty and healthy tissue. It may find new applications in molecular imaging with a new contrast agent (e.g., as discussed in F. Hyafil, J. Cornily, J. E. Feig, R. Gordon, E. Vucic, V. Amirbekian, E. A. Fisher, V. Fuster, L. J. Feldman, and Z. A. Fayad, "Noninvasive detection of macrophages using a nanoparticulate contrast agent for computed tomography", *Nature Medicine,* 13, 636-641, 2007, which is incorporated herein by reference in its entirety). The polynomial approximation methods are widely used in the pre-reconstruction decomposition.

Thus, background methods of dual-energy CT may reconstruct images having reduced beam hardening artifacts by performing pre-reconstruction decomposition. The projections of imaged subjects are related to the line integral of the two basis materials, e.g. bone and water, or two components of photon absorptions, i.e. photoelectric and Compton processes through non-linear equations. Usually, the projections are fitted into polynomials of the line integrals. From the measured projection data, the line integrals can be obtained by solving the polynomials. Other methods, such as the variation method, the sub-region method, and the iso-transmission method can also be used in the decompositions. The basis images then can be generated from the resulting line integrals by a conventional reconstruction algorithm. The effective Z, density, and monochromatic images can be obtained by combining the basis images.

However, as discussed in K. Chuang and H. K. Huang, "Comparison of four dual energy image decomposition methods", *Phys. Med. Biol.,* 33, 455-466, 1988, which is incorporated herein by reference in its entirety, the direct polynomial approximation is not accurate and the indirect polynomial approximation has some computational drawbacks.

In particular, background pre-reconstruction decomposition methods may described as follows:

Polynomial Method

The measured projection data at low and high voltages are written as two polynomials of the line integrals of basis materials. The coefficients in the polynomials are obtained by fitting to the calibration measurements. The line integrals are calculated by use of the Newton-Raphson iteration method.

Direct Polynomial Method

The line integrals of the two basis materials are approximated with two polynomials of the measured projection data. The coefficients in the polynomials are obtained by fitting to the calibration measurements. From the measured projection data, the line integrals can be obtained directly.

Sub-region Method

This method is an improvement of the direct polynomial method. The projections are divided into many sub-regions and the coefficients of the polynomials are tuned up for each sub-region.

Iso-transmission Method

The projection data are written as a linear function of the line integrals. The so called regression coefficients in the function depend on the projection data. These coefficients are predefined on a set of projection values through a calibration procedure. For any projection value within the limit of the calibration table, an interpolation procedure is adopted to obtain the regression coefficients. Finally, the line integrals are obtained by solving the linear equations.

Variation Method

A cost function is defined as a sum of square difference between the measured projection and the predicted projection as a function of line integrals. Finding the minimum of the cost function with certain constraints, one can determine the line integrals.

SUMMARY OF THE INVENTION

To overcome the problems noted above, and other problems, one object of the present inventions is to use the dual energy scans to better handle the nonlinear beam hardening terms, and thereby derive data based on pure line integrals where the exact Radon inversion applies. In particular, the problem may be modeled as a black box, with high and low polychromatic data going into the box (along with a priori knowledge such as spectra and linear attenuation coefficients for two basis materials) and receiving from the box pure line integrals of the two basis materials.

Accordingly, one object of this invention is to provide a novel method of obtaining a computed tomography image of an object. The method includes obtaining object dual-energy projection data of the object; obtaining average attenuation coefficients and non-linear beam hardening coefficients; determining, for the object dual-energy projection data, a pair of line integral equations that, upon introducing the average attenuation coefficients, are reorganized into a pair of reorganized line integral equations including linear terms and non-linear beam hardening terms; obtaining initial solutions of the reorganized line integral equations by setting the non-linear beam hardening terms to zero; iteratively solving the reorganized line integral equations starting with the initial solutions to obtain a first basis line integral solution for a first basis material and a second basis line integral solution for a second basis material; and reconstructing the computed tomography image of the object based on the first basis line integral solution for the first basis material and the second basis line integral solution for the second basis material.

Another object of this invention is to provide a novel apparatus for obtaining a computed tomography image of an object. The apparatus includes a dual-energy projection data obtaining section configured to obtain object dual-energy projection data of the object; a calculating section configured to obtain average attenuation coefficients and non-linear beam hardening coefficients; a line integral determining portion configured to determine, for the object dual-energy projection data, a pair of line integral equations that, upon introducing the average attenuation coefficients, are reorganized into a pair of reorganized line integral equations including linear terms and non-linear beam hardening terms; an initial value obtaining section configured to obtain an initial solution of the reorganized line integral equations by setting the non-linear beam hardening terms to zero; an iteratively solving section configured to iteratively solve the reorganized line integral equations starting with the initial solutions to obtain a first basis line integral solution for a first basis material and a second basis line integral solution for a second basis material; and a reconstructing section configured to reconstruct the computed tomography image of the object based on the first basis line integral solution for the first basis material and the second basis line integral solution for the second basis material.

A further object of this invention is to provide a novel computer-readable medium having computer program instructions that, when executed by a computer, cause the computer to perform steps of obtaining a computed tomography image of an object. The steps include obtaining object dual-energy projection data of the object; obtaining average attenuation coefficients and non-linear beam hardening coefficients; determining, for the object dual-energy projection data, a pair of line integral equations that, upon introducing the average attenuation coefficients, are reorganized into a pair of reorganized line integral equations including linear terms and non-linear beam hardening terms; obtaining initial solutions of the reorganized line integral equations by setting the non-linear beam hardening terms to zero; iteratively solving the reorganized line integral equations starting with the initial solutions to obtain a first basis line integral solution for a first basis material and a second basis line integral solution for a second basis material; and reconstructing the computed tomography image of the object based on the first basis line integral solution for the first basis material and the second basis line integral solution for the second basis material.

Another object of this invention is to provide a novel method for obtaining a computed tomography image of an object. The method includes obtaining object dual-energy projection data of the object; obtaining phantom dual-energy projection data of a phantom including the first basis material and the second basis material. Most of an attenuation by the first basis material in the phantom dual-energy projection data corresponds to a photoelectric attenuation process, and most of an attenuation by the second basis material in the dual-energy projection data corresponds to a Compton attenuation process. The method also includes reconstructing the computed tomography image of the object based on a first basis line integral solution for the first basis material and a second basis line integral solution for the second basis material.

Another object of this invention is to provide a novel apparatus for obtaining a computed tomography image of an object. The apparatus includes a dual-energy projection data obtaining section configured to obtain object dual-energy projection data of the object; and a calibration section configured to obtain phantom dual-energy projection data of a phantom including the first basis material and the second basis material. Most of an attenuation by the first basis material in the phantom dual-energy projection data corresponds to a photoelectric attenuation process, and most of an attenuation by the second basis material in the dual-energy projection data corresponds to a Compton attenuation process. The apparatus also includes a reconstructing section configured to reconstruct the computed tomography image of the object based on a first basis line integral solution for the first basis material and a second basis line integral solution for the second basis material.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
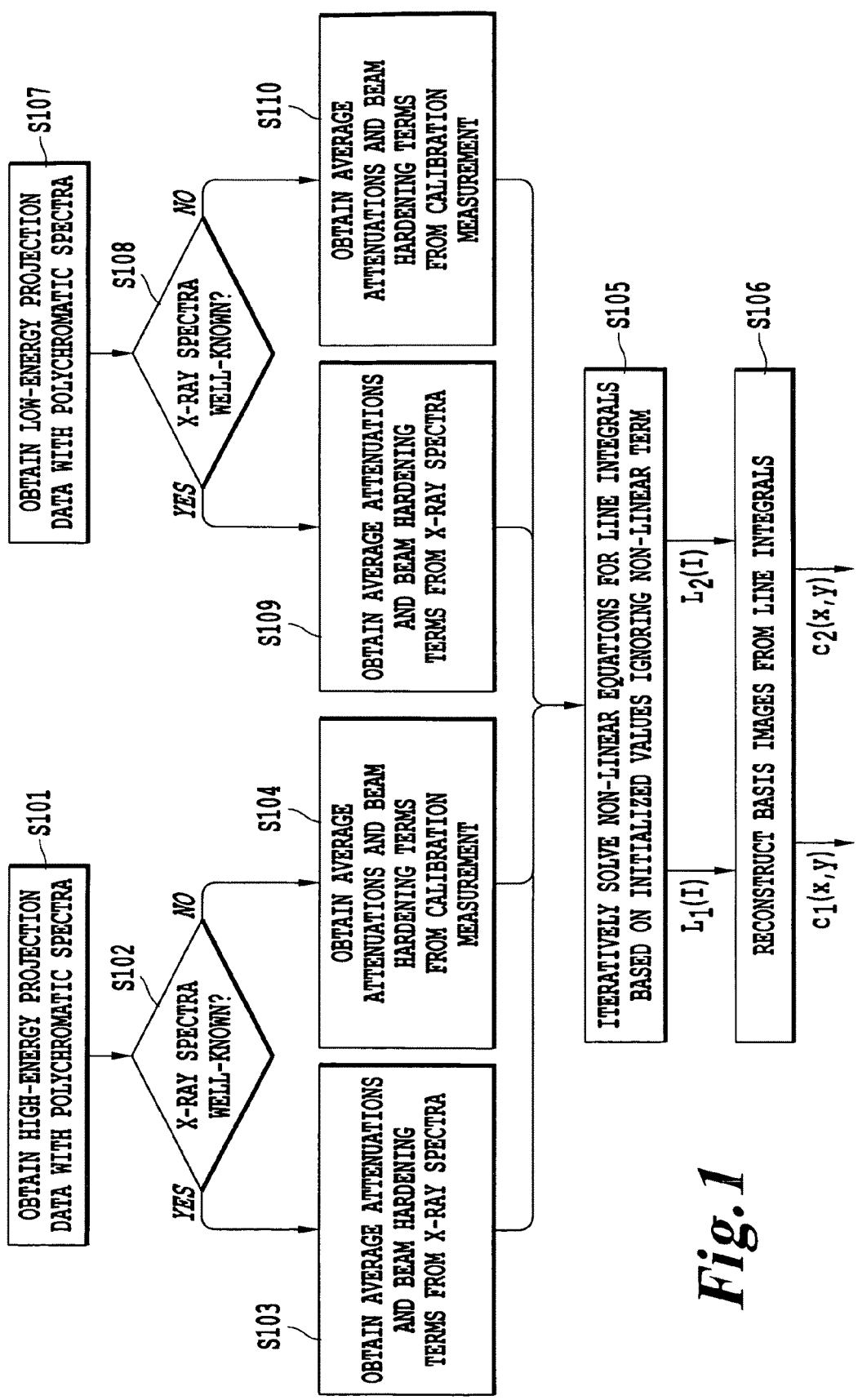
FIG. 1 is a flow diagram of a method according to an embodiment of the present invention.

Conventional methods of dual-energy CT image reconstruction may perform slowly and be difficult or expensive to implement. For example, the polynomial fitting method may introduce some errors and the inversion method has some computational drawbacks, the variation method is computationally time consuming, and the sub-region and iso-transmission methods are more sensitive to noise. Further, implementations of those methods may be complex.

The present invention includes 1) a new pre-reconstruction decomposition method and 2) an approach to obtain parameters through a calibration in cases where the spectra are not well known. A numerical simulation study demonstrates that the methods are accurate, stable, and efficient. No significant noise amplification was observed in an experimental monochromatic image at proper energies.

According to an embodiment of the present invention, a pre-reconstruction decomposition method includes rewriting the non-linear equations as linear terms combined with non-linear beam-hardening terms, and an iterative approach is adopted to solve the equations. Since the linear terms are dominant, the iterations converge stably and rapidly. A calibration method may be used to obtain the parameters in the non-linear equations in the case that the x-ray spectra are not well known. Thus, an embodiment of the present invention may generally include the following four steps:

1) Divide the projections measured with polychromatic spectra into linear parts and beam hardening non-linear parts with respect to the line integrals, 2) Obtain the average attenuations and beam hardening terms from x-ray spectra or through a calibration measurement, 3) Solve the non-linear equations for the line integrals iteratively starting from ignoring the non-linear terms, and 4) Reconstruct the basis images from the line integrals with a conventional reconstruction algorithm.

Referring now to the drawings, wherein like reference numerals designate identical or corresponding parts throughout the several views.

FIG. 1 is a flow diagram of an embodiment of the present invention that includes obtaining projection data with polychromatic spectra. In particular, high-energy projection data is obtained in step S101, and low-energy projection data is obtained in step S107. The values produced by step S101 corresponds to $g_H(l)$ in equation (6) below. The values produced by step S107 corresponds to $g_L(l)$ in equation (6) below. According to S102, for the high-energy projection data, if the x-ray spectra are well known, the method continues with step S103, and if the x-ray spectra are not well known, the method continues with step S104. Similarly, according to S108, for the low-energy projection data, if the x-ray spectra are well known, the method continues with step S109, and if the x-ray spectra are not well known, the method continues with step S110. In steps S103 and S109, average attenuations and beam hardening terms are obtained from the well known x-ray spectra. In steps S104 and S110, average attenuations and beam hardening terms are obtained from one or more calibration measurements. In this example, there are four average attenuations used (see equation 8 below): a high spectrum average over basis material 1, a high spectrum average over basis material 2, a low spectrum average over basis material 1, and a low spectrum average over basis material 2. The values produced by steps S103 and S104 correspond to $g_H(l)$ in equation (11) below. The values produced by steps S109 and S110 correspond to $g_L(l)$ in equation (11) below. In step S105, non-linear equations are iteratively solved to obtain line integrals $L_1(l)$ for a first basis material and $L_2(l)$ for a second basis material. In the first iteration, the non-linear equations are initialized using values independent of the non-linear terms, which are ignored. After the iterative process yields a solution to the line integrals, the basis images $c_{1,2}(x,y)$ are reconstructed from the line integrals in step S106.

Thus, in this example, dual-energy projection data of an object is obtained. A pair of line integral equations (e.g., equations 5 below) for the dual-energy projection data are obtained. The equations are such that upon introducing average attenuation terms (e.g., H, L, 1, and 2 in equation 8), the equations may be reorganized into including linear terms and non-linear beam hardening terms. Next, the line integral equations may be iteratively solved.

Figure 2:
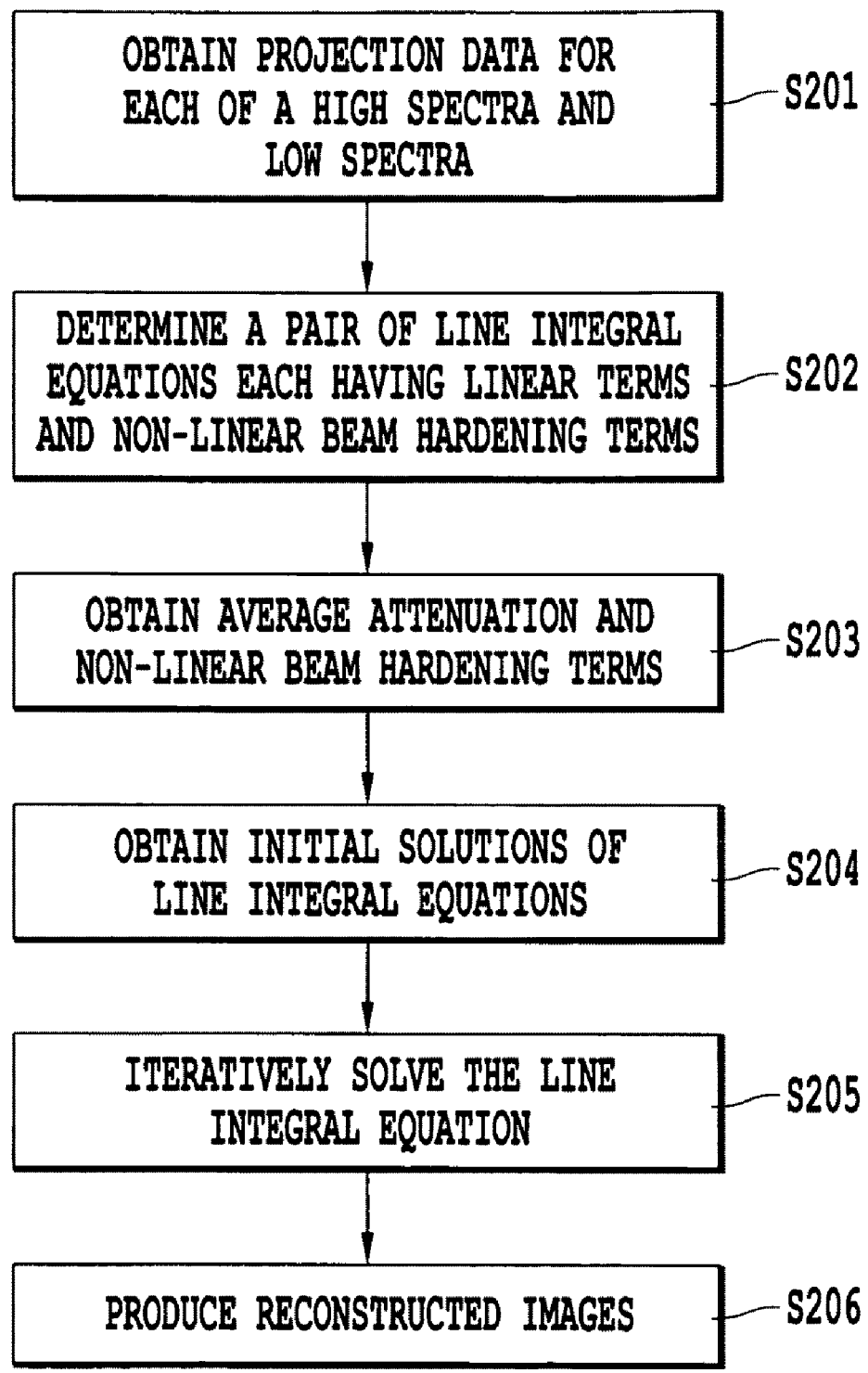
FIG. 2 is a flow diagram of a method according to an embodiment of the present invention.

FIG. 2 is a flow diagram of an embodiment of the present invention. In step S201, projection data of an object is obtained for high energy spectra and low energy spectra. In step S202, a pair of line integral equations each having a linear term and a non-linear beam hardening term are determined. In step S203, average attenuation terms and beam hardening terms are obtained. In step S204, initial solutions of the line integral equations are obtained. In step S205, the line integral equations are solved iteratively, and in step S206, a reconstructed image of the object is produced based on combined pre-reconstruction decomposition data.

Depending on clinical application, the basis material images can be used directly, the basis material images can be combined to produce monochromatic images at any selectable energy, or the basis material images can be combined to give density and effective atomic number maps of a patient's tissues, for example.

For example, the basis material images can be combined to produce monochromatic images, density images, or effective atomic number maps according to the following equations:

For monochromatic images:

$$\mu(E,x,y) = \mu_1(E)c_1(x,y) + \mu_2(E)c_2(x,y).$$

For density images:

$$\rho_{Map}(x,y) = \frac{1000}{\rho_{H_2O}}(\rho(x,y) - \rho_{H_2O})$$

with $$\rho(x,y) = \rho_1 c_1(x,y) + \rho_2 c_2(x,y),$$

where rho is density.

For effective atomic number:

$$Z_{map}(x,y) = \frac{1000}{Z_{H_2O}}(Z_{eff}(x,y) - Z_{H_2O})$$

$$Z_{eff}(x,y) = \left[\frac{\rho_1 c_1(x,y)Z_1^{4.4} + \rho_2 c_2(x,y)Z_2^{4.4}}{\rho_1 c_1(x,y) + \rho_2 c_2(x,y)}\right]^{1/4.4}.$$

Figure 3:
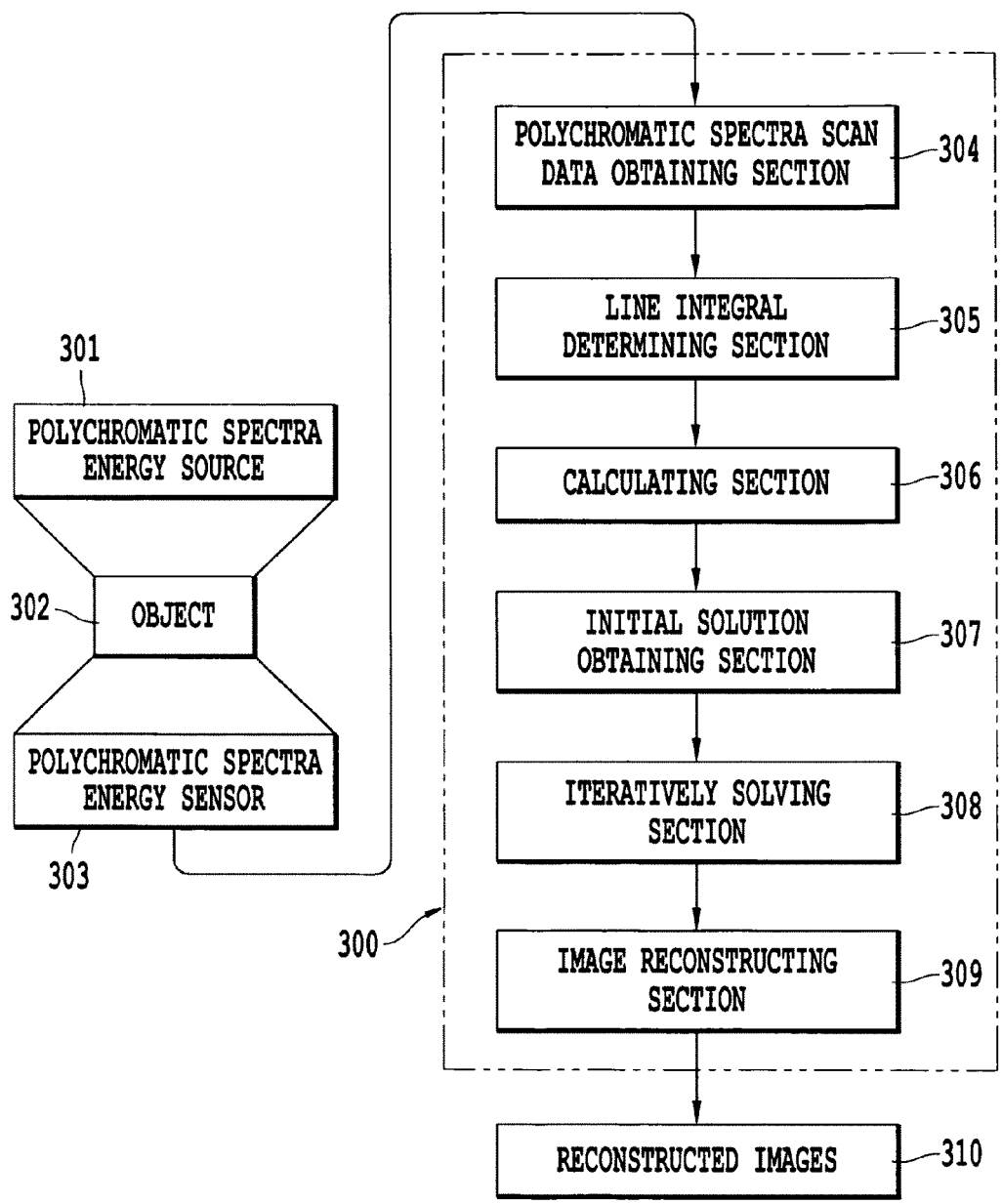
FIG. 3 is a block diagram of an apparatus according to an embodiment of the present invention.

FIG. 3 is a block diagram of an embodiment of the present invention, including a pre-reconstruction decomposition apparatus 300 that may produce a reconstructed image 310.

According to the embodiment of FIG. 3, the pre-reconstruction decomposition apparatus 300 includes a polychromatic spectra scan data obtaining section 304, a line integral determining section 305, a calculating section 306, an initial value obtaining section 307, an iteratively solving section 308, and an image reconstruction section 309. The polychromatic spectra scan data obtaining section 304 is configured to obtain scan data of an object 302 from a polychromatic spectra energy sensor 303 that detects energy from a polychromatic spectra energy source 301 passing through the object 302, or from a stored data source (not shown). Further, as discussed above and depending on clinical application, the basis material images can be used directly, the basis material images can be combined to produce monochromatic images at any selectable energy, or the basis material images can be combined to give density and effective atomic number maps of a patient's tissues.

Although the embodiment of the invention in FIG. 3 is shown as a combination of sections, one of skill in the art would recognize that the invention may be implemented using a combination of function specific hardware or software elements, or a combination of general purpose elements implemented using programmable hardware devices or software sections. Program instructions for such software sections may be stored on a computer-readable medium and executed by a computer.

The following notation is used in descriptions of embodiments of the invention below E energy variable H,L labels for high and low energy spectra $S(E), S_{H,L}(E)$ energy-weighted x-ray spectra.

l integration path. This can be designated (in 2D CT) by a view and channel indices: $\beta, \gamma$ I(l) transmitted intensity along path l $\mu(E,x,y)$ the energy-dependent linear attenuation coefficient of tissues at voxel x,y $\bar{\mu}_{1,2}^{H,L}$ linear attenuation coefficient for basis material 1 or 2 averaged over the high (H) or low (L) spectrum.

$\mu_{PE,i}(E), \mu_{C,i}(E)$ the photoelectric and Compton linear attenuation coefficients of tissue i $\mu_1(E), \mu_2(E)$ the linear attenuation coefficients of basis materials 1 and 2, known functions of photon energy $g_{H,L}(l)$ projection datum with high or low spectra along path l $c_{1,2}(x,y)$ how much the tissue at voxel x, y is like basis material 1 or 2, independent of energy $L_{1,2}(l)$ the line integral of $c_{1,2}(x,y)$ along path l z atomic number of an element or effective atomic number of a tissue type. The effective atomic number is given by $$Z = \frac{\sum_i n_i M_i Z_i}{\sum_i M_i},$$

where $Z_i$ is the atomic number of the $i^{th}$ element, $M_i$ is the atomic mass, and $n_i$ is the number of atoms of the $i^{th}$ element. Water has a Z of 7.22.

Other notation is introduced in the description below as needed. $C_{1,2}(x,y)$ and $L_{1,2}(l)$ are independent of E. The mass attenuation coefficients are independent of voxel location. Further, detectors used with embodiments of the present invention measure energy deposited so S is the photon number at each energy multiplied by the energy.

Also, because a bow-tie filter is used, S depends on channel $\gamma$ (or path l); this dependency is omitted from further equations, although it should be understood that the dependency exists. In addition, the spectra are assumed normalized. That is, $\int S_{H,L}(E)dE=1$.

The transmitted intensity is given by $$I(l)=\int S(E)\exp[-\int_l \mu(E,x,y)dl]dE. \quad (1)$$

The attenuation coefficients may be understood as a sum of their physical processes. In the diagnostic energy range, the two dominate physical processes are photoelectric (PE) and Compton (C). Thus, we can write $$\mu(E,x,y)=\mu_{PE}(E,x,y)+\mu_C(E,x,y). \quad (2)$$

To factorize the energy and spatial dependencies of the linear attenuation coefficient, Eqn. (2) is rewritten as $$\mu(E, x, y) = \sum_i \delta_{i,j(x,y)}(\mu_{PE,i}(E) + \mu_{C,i}(E)), \quad (3)$$

where the sum goes over all tissue types labeled by i. The interpretation of Eqn. (3) is that at a given location x,y, the tissue is type $$j, \delta_{i,j} = \begin{cases} 1 & \text{if } i = j \\ 0 & \text{if } i \neq j \end{cases}.$$

Next, the photoelectric and Compton are replaced by two basis materials, one of which acts more like photoelectric (relatively high Z) and one of which acts more like Compton (relatively low Z). Therefore, the linear attenuation coefficients of tissues in an object (e.g., a patient) can be expanded into two basis functions:

$$\mu(E,x,y)\approx\mu_1(E)c_1(x,y)+\mu_2(E)c_2(x,y) \quad (4)$$

where $c_{1,2}(x,y)$ represent how much the voxel at x, y is like basis material 1 and 2, respectively. This hypothesis is a good approximation as long as:

the energy of the K-edge of any tissue of interest is not in the energy range where the two spectra $S_{H,L}$ are not small and two basis coefficients have different enough energy dependence in the energy range of interest.

Even for a material whose K-edge is within this range such as iodine, the introduced error may be small enough to be ignored.

Figure 9:
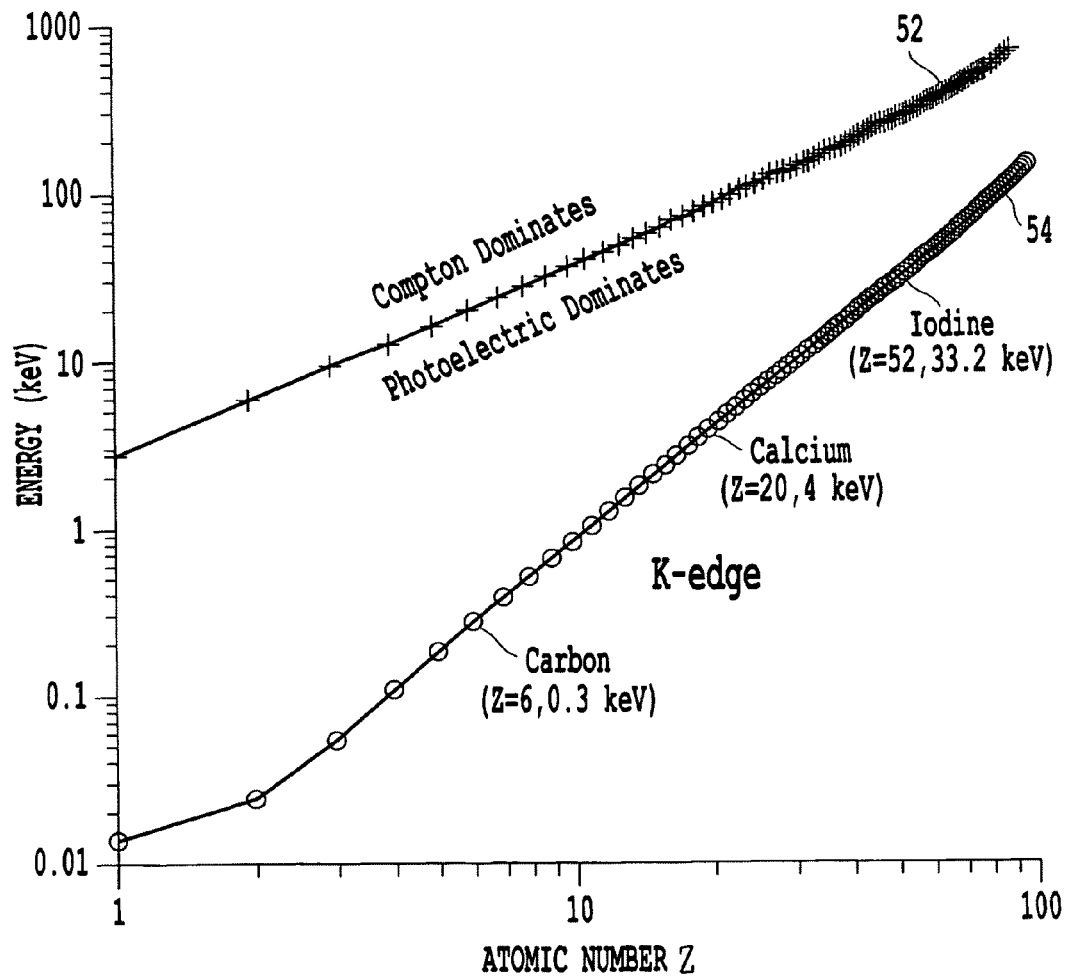
FIG. 9 is a graph of energy vs. atomic number.

FIG. 9 is a graph that shows the K-edge location for all the elements, and is described further below.

It is preferred that $\mu_1$ and $\mu_2$ have different energy dependencies. The energy dependence of photoelectric and Compton interactions are complicated functions of energy. In the diagnostic energy range, photoelectric goes approximately as $E^{-3}$ while Compton is fairly flat. High Z materials are dominated by photoelectric (depending on the energy, about $Z^4$), while low Z materials are dominated by Compton. See FIG. 9 below.

Also, linear attenuation coefficients for the basis coefficients are independent of location and are known. Inserting Eqn. (4) into Eqn. (1) results in one equation with two unknowns: $c_1(x,y), c_2(x,y)$. Therefore, projection data may be obtained using at least two different spectra, at high (H) and low (L), to obtain two equations and two unknowns and potentially solve for the unknowns. The resulting equations are:

$$I_H(l) = \int S_H(E) \exp\left[-\mu_1(E) \int_l c_1(x,y) dl - \mu_2(E) \int_l c_2(x,y) dl\right] dE \quad (5)$$

$$I_L(l) = \int S_L(E) \exp\left[-\mu_1(E) \int_l c_1(x,y) dl - \mu_2(E) \int_l c_2(x,y) dl\right] dE.$$

The linear attenuation coefficients are removed from the line path integrals in Eqn. (5). Now the projection data may be formed by taking the logs:

$$g_H(l) = -\ln \int S_H(E) \exp[-\mu_1(E) L_1(l) - \mu_2(E) L_2(l)] dE \quad (6)$$

$$g_L(l) = -\ln \int S_L(E) \exp[-\mu_1(E) L_1(l) - \mu_2(E) L_2(l)] dE,$$

where $g_L$, $g_H$ are logarithm of the normalized intensity after attenuation through the patient from spectra $S_L$, $S_H$, respectively and $L_1$, $L_2$ are line integrals of $c_1$, $c_2$. Eqn. (6) includes the notation:

$$L_2(l) = \int_l c_{1,2}(x,y) dl. \quad (7)$$

An intermediate goal in this embodiment of the invention is to solve the two equations in (6) for $L_{1,2}$ and then to reconstruct $c_{1,2}(x,y)$ by standard CT reconstruction techniques.

Eqns. (6) are solved for $L_{1,2}$ by linearizing each equation and treating the rest as perturbative beam-hardening terms that are best handled by iterative solution (as shown below). If the beam-hardening terms are relatively small, the solutions are expected to converge quickly and stably. Define $$\bar{\mu}_{1,2}^{H,L} = \int S_{H,L}(E) \mu_{1,2}(E) dE \quad (8)$$

as the energy averaged linear attenuation coefficient, and $$\Delta\mu_{1,2}^{H,L}(E) = \mu_{1,2}(E) - \bar{\mu}_{1,2}^{H,L} \quad (9)$$

as the difference from the average. Note that $\bar{\mu}$ is a function of path because the spectra are a function of path due to the bow-tie filter. Insert Eqn. (9) into Eqns. (6)

$$g_H(l) = -\ln \int S_H(E) \quad (10)$$
$$\exp[-\bar{\mu}_1^H L_1(l) - \Delta\mu_1^H(E) L_1(l) - \bar{\mu}_2^H L_2(l) - \Delta\mu_2^H(E) L_2(l)] dE$$

$$g_L(l) = -\ln \int S_L(E) \exp[-\bar{\mu}_1^L L_1(l) - \Delta\mu_1^L(E) L_1(l) -$$
$$\bar{\mu}_2^L L_2(l) - \Delta\mu_2^L(E) L_2(l)] dE.$$

These simplify to $$g_H(l) = \bar{\mu}_1^H L_1(l) + \bar{\mu}_2^H L_2(l) - g_H^{(BH)}(L_1(l), L_2(l)) \quad (11)$$
$$g_L(l) = \bar{\mu}_1^L L_1(l) + \bar{\mu}_2^L L_2(l) - g_L^{(BH)}(L_1(l), L_2(l)),$$

where $$g_{H,L}^{(BH)}(L_1(l), L_2(l)) \equiv \ln \int S_{H,L}(E) \exp[-L_1(l)\Delta\mu_1^{H,L}(E) - L_2(l)\Delta\mu_2^{H,L}(E)] dE \quad (12)$$

is the beam hardening perturbation.

For two monochromatic spectra, $\Delta\mu_{1,2}^{H,L}$ are 0 and $g_{H,L}^{(BH)}$ are 0. Eqn. (11) can then be solved analytically for $L_{1,2}$. Using a matrix approach:

$$\begin{pmatrix} g_H \\ g_L \end{pmatrix} = \begin{pmatrix} \bar{\mu}_1^H & \bar{\mu}_2^H \\ \bar{\mu}_1^L & \bar{\mu}_2^L \end{pmatrix} \begin{pmatrix} L_1 \\ L_2 \end{pmatrix} \quad (13)$$

solving for $L_{1,2}$ by taking the inverse, we get $$\begin{pmatrix} L_1 \\ L_2 \end{pmatrix} = D^{-1} \begin{pmatrix} \bar{\mu}_2^L & -\bar{\mu}_2^H \\ -\bar{\mu}_1^L & \bar{\mu}_1^H \end{pmatrix} \begin{pmatrix} g_H \\ g_L \end{pmatrix} \quad (14)$$

where D is the determinant of the 2×2 matrix in Eqn. (13), $$D = \bar{\mu}_1^H \bar{\mu}_2^L - \bar{\mu}_1^L \bar{\mu}_2^H \quad (15)$$

In the present embodiment of the invention, it is preferred that the determinant not be near 0 to avoid an unstable solution. The determinant approaches 0 if:

L→H: that is, there is little separation between the high and low spectra,

Material 1→material 2; that is, $$\frac{\bar{\mu}_1^H}{\bar{\mu}_1^L} \approx \frac{\bar{\mu}_2^H}{\bar{\mu}_2^L}:$$

The energy attenuation ratios of two tissues are too similar: the two tissues have the same attenuation behavior as a function of energy.

For the polychromatic case, the matrix version of Eqn. (11) can be written as $$\begin{pmatrix} g_H - g_H^{(BH)}(L_1, L_2) \\ g_L - g_L^{(BH)}(L_1, L_2) \end{pmatrix} = \begin{pmatrix} \bar{\mu}_1^H & \bar{\mu}_2^H \\ \bar{\mu}_1^L & \bar{\mu}_2^L \end{pmatrix} \begin{pmatrix} L_1 \\ L_2 \end{pmatrix} \quad (16)$$

Solve these iteratively with n as the iteration number for $L_{1,2}$:

$$\begin{pmatrix} L_1^n \\ L_s^n \end{pmatrix} = D^{-1} \begin{pmatrix} \bar{\mu}_2^L & -\bar{\mu}_2^H \\ -\bar{\mu}_1^L & \bar{\mu}_1^H \end{pmatrix} \begin{pmatrix} g_H - g_H^{(BH)}(L_1^{n-1}, L_2^{n-1}) \\ g_L - g_L^{(BH)}(L_1^{n-1}, L_2^{n-1}) \end{pmatrix}. \quad (17)$$

The initial estimate for $L_{1,2}^0$ is given by the linear equation without the beam hardening terms, Eqn. (14). Finally, the solution may be based on the previous estimates for $L_{1,2}$, the high and low energy spectra, and the linear attenuation coefficients of the basis materials. Thus, an updated estimate for $g_{H,L}^{(BH)}$ may be obtained and used to solve for the updated $L_{1,2}$ using Eqn. (17) with the measured projections $g_{H,L}$.

According to this embodiment of the invention, Eqns. (6) may be solved for $L_{1,2}$. Standard reconstruction techniques such as Filtered Back-Projection (FBP) or True Cone beam Tomography (TCOT) may be used to solve for $c_1(x,y)$ and $c_2(x,y)$. The image maps for $c_1(x,y)$ and $c_2(x,y)$ are not in Hounsfield Units (HU). We get HU by applying the linear superposition of the basis maps via Eqn. (4), where now we can pick any E we want. The result is the beam hardened corrected image at the chosen monochromatic energy E. Alternatively, density and effective atomic number images can be obtained by applying a non-linear superposition of the basis maps. Note that in this discussion, the terms images and maps are used interchangeably.

Calibration

It is preferred to obtain the beam hardening terms and the average attenuations $\bar{\mu}_i^{(x)}$ from calibrations instead of the two spectra because it may be difficult to measure the spectra accurately. With a step phantom composed by two basis materials, the projections $g_x(L_1, L_2)$ may be measured for a specific spectrum x=L,H. For projections without material 2, we have $$\bar{\mu}_1^{(x)} L_1 = g_x(L_1, 0) + g_x^{(BH)}(L_1, 0). \quad (18)$$

From Eq. (5a,b), we have $g_x^{(BH)}(L_1, 0) \sim O(L_1^2)$. Therefore, the average attenuations may be obtained by $$\bar{\mu}_1^{(x)} = \lim_{L_1 \to 0} \frac{g_x(L_1, 0)}{L_1}. \quad (19)$$

If ΔL represents an interval of the step wedge, then the constant approximation gives $$\bar{\mu}_1^{(x)} \approx \frac{g_x(\Delta L, 0)}{\Delta L}, \quad (20)$$

and the linear approximation yields $$\bar{\mu}_1^{(x)} \approx \frac{4 g_x(\Delta L_1, 0) - g_x(2\Delta L_1, 0)}{2\Delta L_1}. \quad (21)$$

The same method may be applied to material 2 to determine $\bar{\mu}_2^{(x)}$. Then, the beam hardening term can be obtained by $$g_x^{(BH)}(L_1, L_2) = \bar{\mu}_1^{(x)} L_1 + \bar{\mu}_2^{(x)} L_2 - g_x(L_1, L_2) \quad (22)$$

Decomposition

Figure 4:
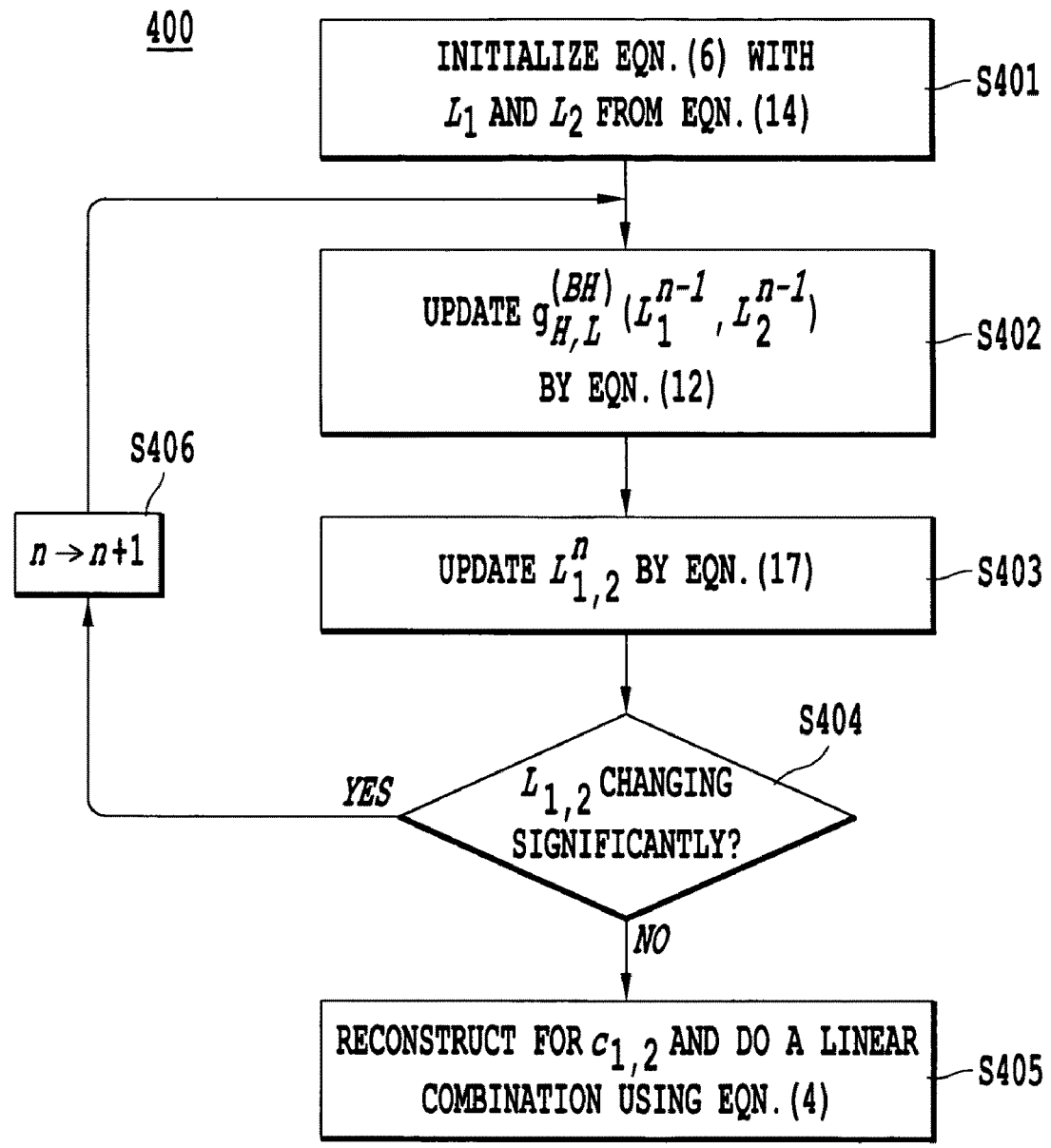
FIG. 4 is a flow diagram of an iterative solution according to an embodiment of the present invention.

FIG. 4 is a flow diagram of a method according to an embodiment of the present invention. In the embodiment of FIG. 4, Eqn. (6) is solved iteratively. In step S401, Eqn. (6) is initialized with $L_{1,2}$ from Eqn. (14). In step S402, Eqn. 12 is solved based on the results of step S401. In step S403, Eqn. (17) is solved based on the results of step S402. In step S404, if the result of step S403 has change significantly since the last iteration, the method continues with step S406, which increments an iteration count n, and then returns to step S402. If the result of step S403 has not changed significantly, the method proceeds to step S405. In step S405, the image is reconstructed using Eqn. (4) based on a linear combination of the linear and beam-hardening portions.

Experimental Results

Calibration

A numerical simulation was performed to evaluate the decomposition and calibration methods using two spectra with tube voltages of 80 kV and 135 kV and using bone and water as the basis materials. With the known model spectra, the projections of $g_x(L_1, L_2)$ were simulated for different thickness of bone $L_1$ and water $L_2$.

Figure 5A:
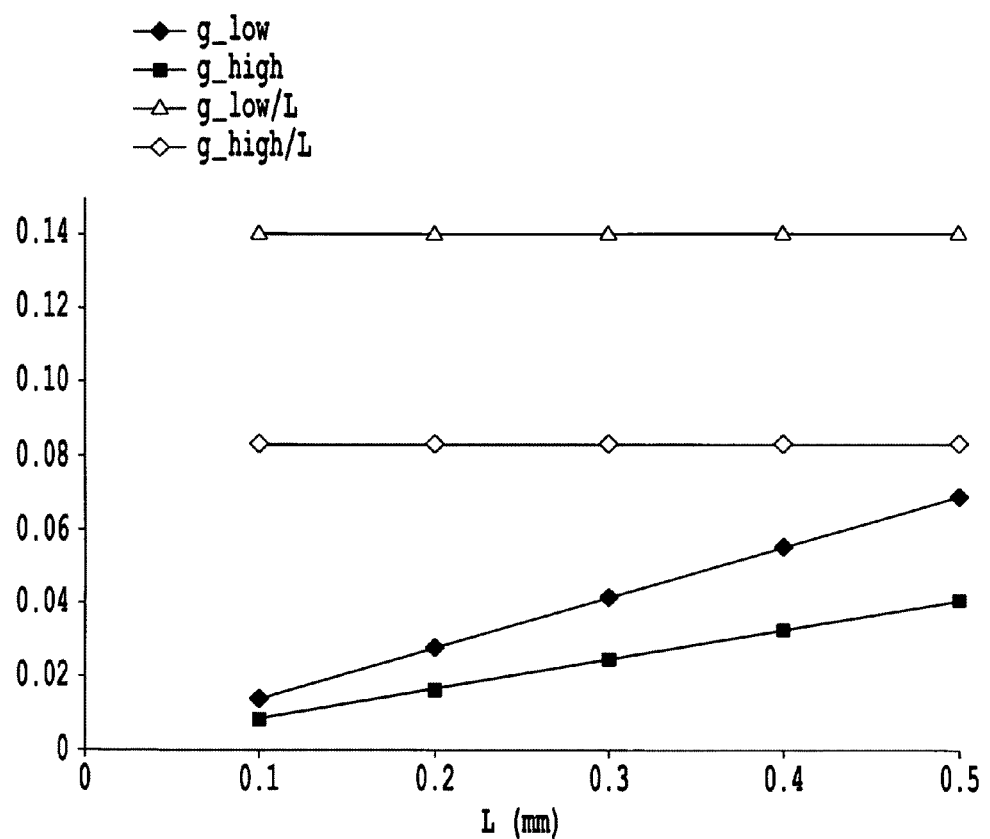
FIG. 5A is a graph of projections of bone for various pathlengths.
Figure 5B:
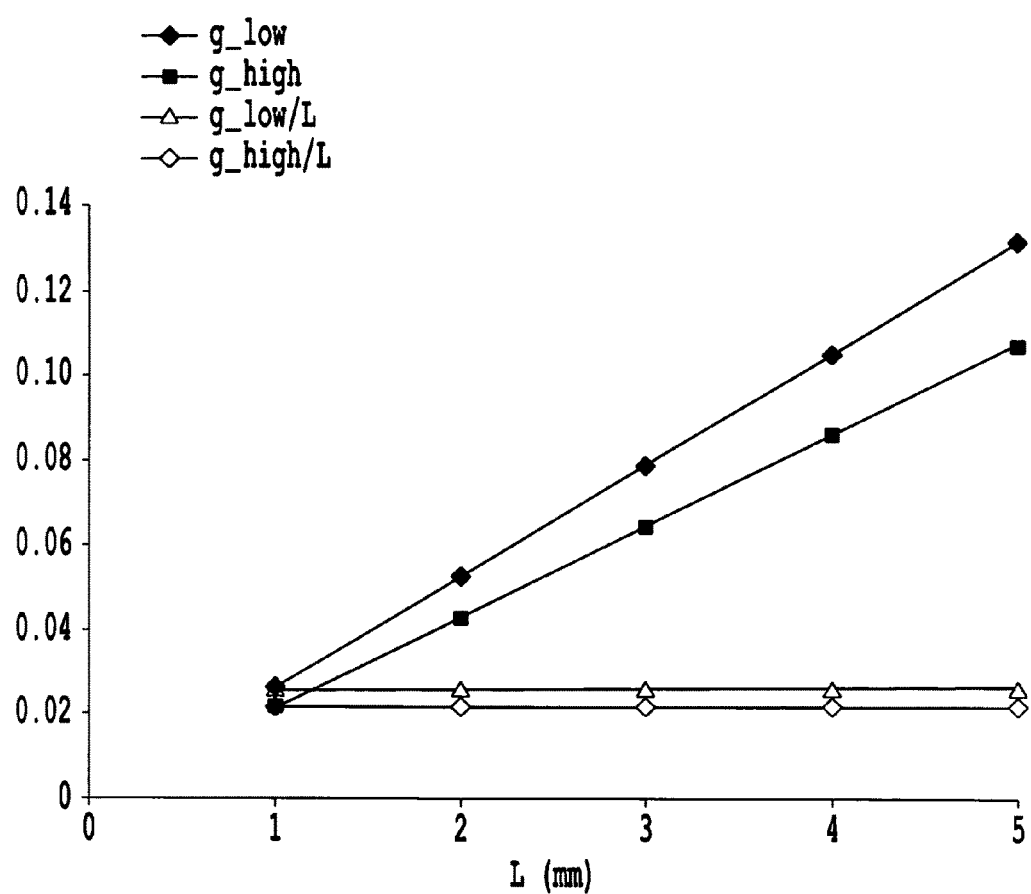
FIG. 5B is a graph of projections of water for various pathlengths.

FIGS. 5A and 5B show the projections of pure basis materials for various pathlengths for low and high energy spectra. FIG. 5A shows the projection for bone and FIG. 5B shows the projection for water. The ratio of the projection to pathlength is nearly constant in the region.

Figure 6A:
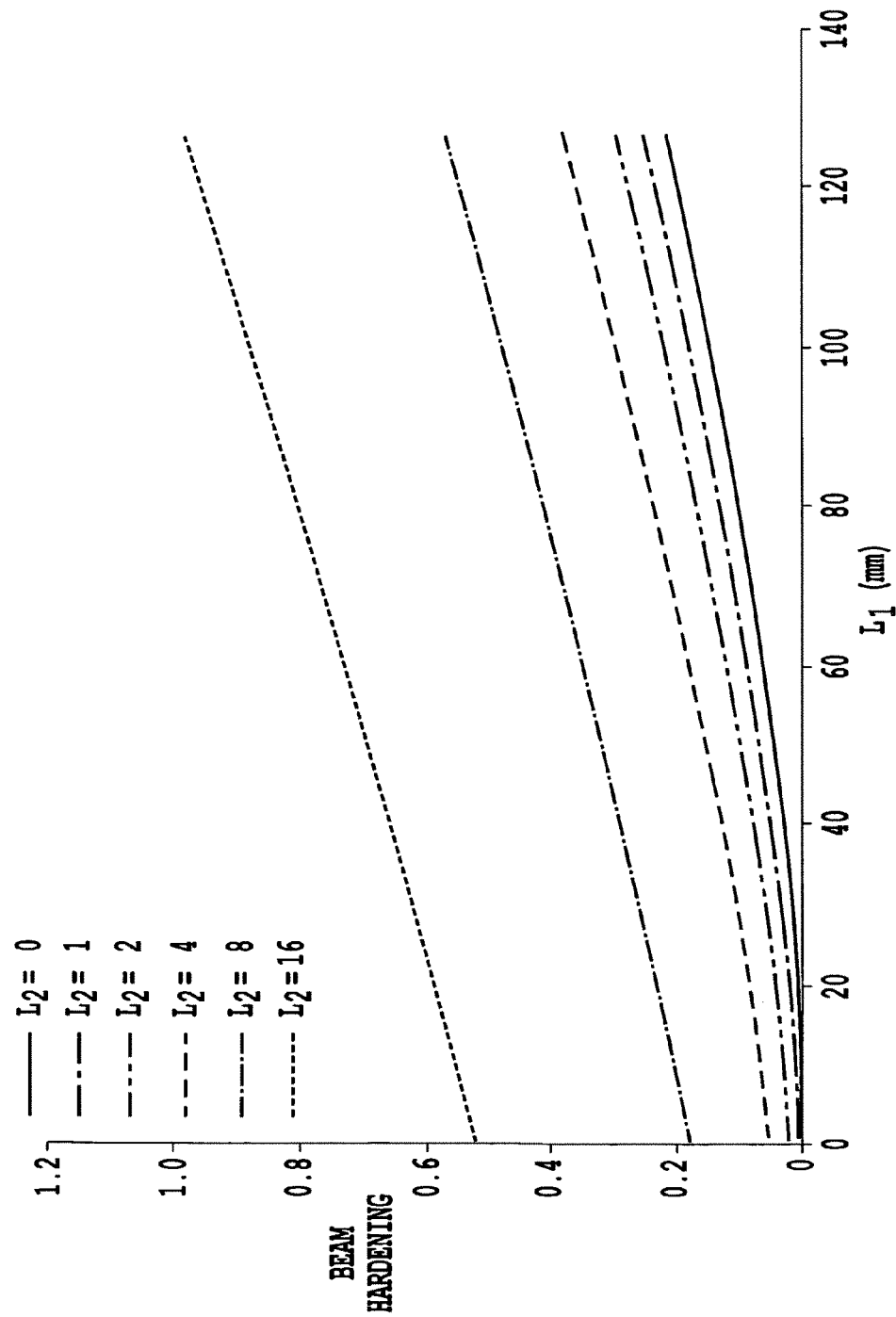
FIG. 6A is a graph of beam-hardening terms using a low energy spectrum.
Figure 6B:
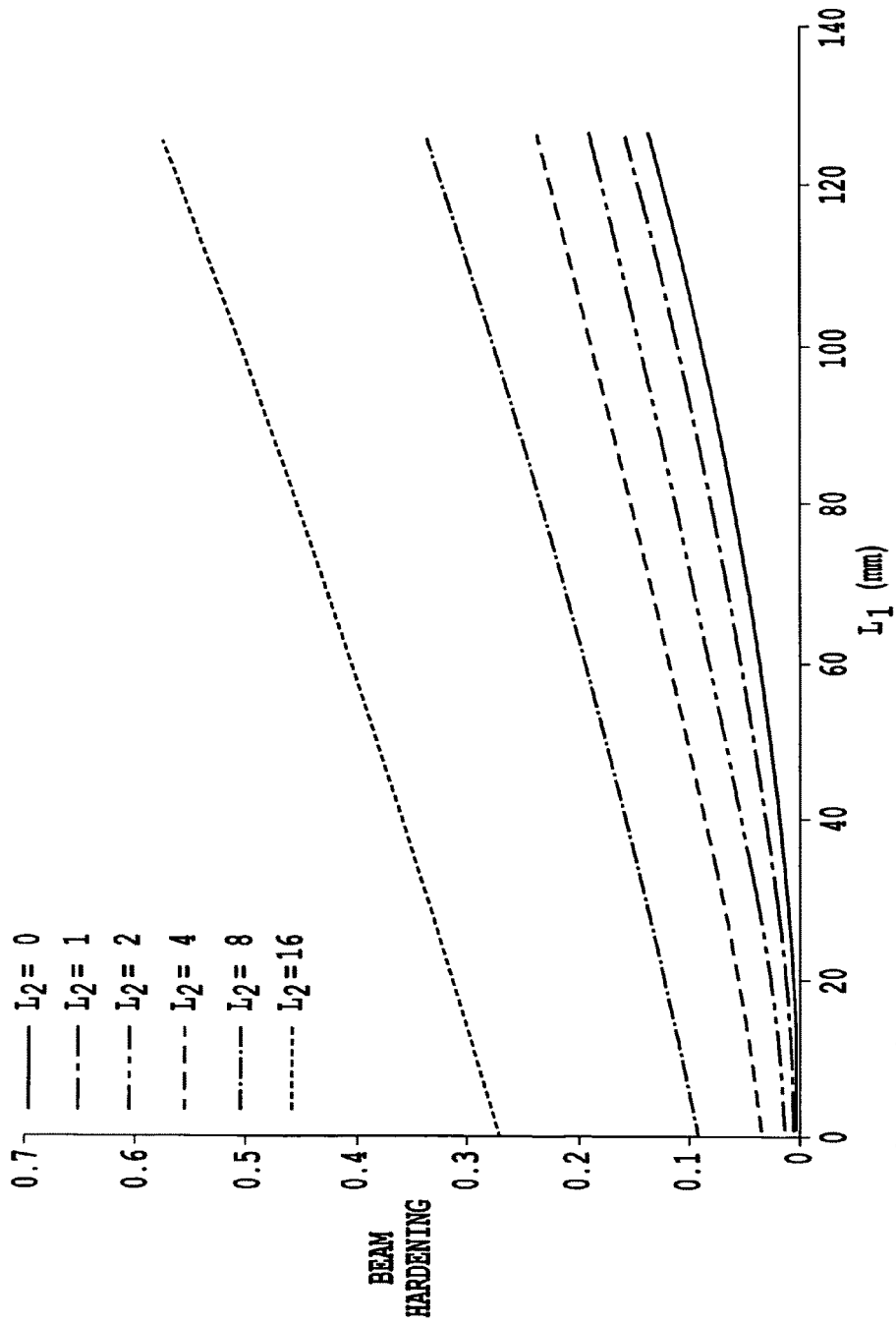
FIG. 6B is a graph of beam-hardening terms using a high energy spectrum.

FIGS. 6A and 6B show beam hardening terms for basis materials. FIG. 6A shows beam hardening terms using the low energy spectrum and FIG. 6B shows beam hardening terms using the high energy spectrum.

Table 1 lists the parameters from known spectra and calibration. With a small thickness of a step phantom, 0.1 mm for bone and 1 mm for water, the average attenuations from known spectra and calibration are essentially same. For practical reason, a step of 4 mm examined, although the invention is applicable to other step sizes. Although the average attenuations are not accurate, they are compensated by the beam hardening terms displayed in FIGS. 6A and 6B using Eqn. (22). The reconstructed images show no artifacts.

TABLE 1

Average attenuations of basis materials for low and high tube voltages ($mm^{-1}$)

|  | 80 kV | 135 kV | 80 kV | 135 kV |
| --- | --- | --- | --- | --- |
|  | Bone (0.1 mm) | | Water (1 mm) | |
| Spectra | 0.142245 | 0.082684 | 0.025998 | 0.021324 |
| Cali. (const) | 0.141412 | 0.082359 | 0.025958 | 0.021306 |
| Cali. (linear) | 0.142216 | 0.082681 | 0.025997 | 0.021323 |
|  | Bone (4 mm) | | Water (4 mm) | |
| Cali. (linear) | 0.121913 | 0.074717 | 0.025959 | 0.021309 |

Decomposition

With a numerical phantom composed of bone, water and blood, polychromatic projection data were generated for the two different spectra with or without noise at tube voltages of 80 kV and 135 kV. In decomposition, we solve Eqns. (11) iteratively starting from ignoring the beam hardening terms.

Figure 7C:
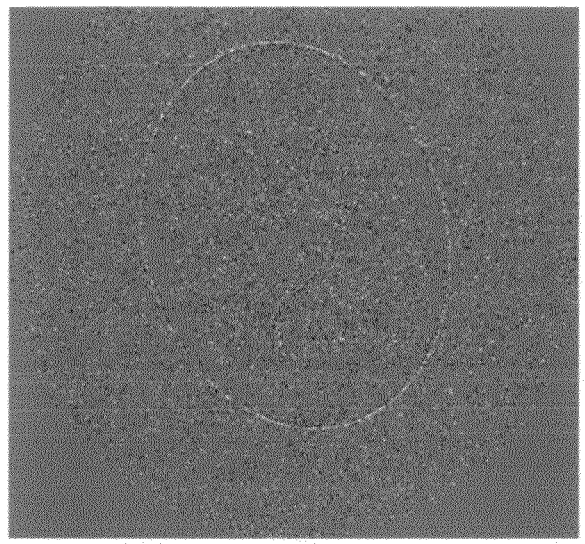
FIG. 7C is a difference image showing a difference of the known spectra image in FIG. 7A and the calibration image in FIG. 7B.
Figure 7B:
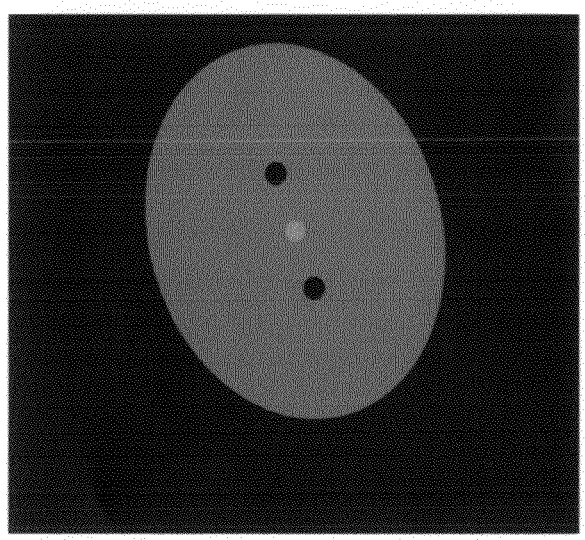
FIG. 7B is a reconstructed water component image from calibration data.
Figure 7A:
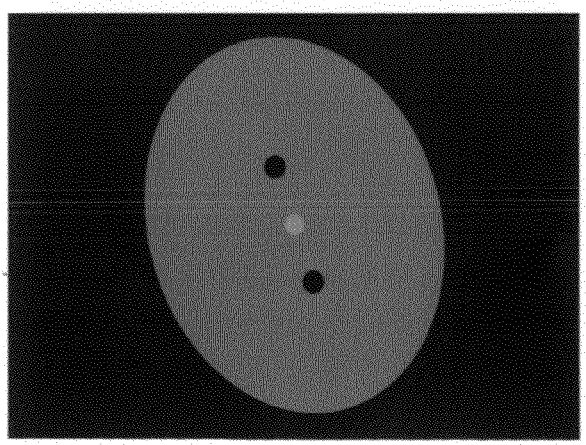
FIG. 7A is a reconstructed water component image from a known spectra.

FIGS. 7A-7C show reconstructed water component images. FIG. 7A shows reconstructed water component image from a known spectra. FIG. 7B shows reconstructed water component image from calibration. FIG. 7C shows a difference of the known spectra image in FIG. 7A and the calibration image in FIG. 7B. There is no significant difference between the images from known spectra and from calibration.

Figure 8B:
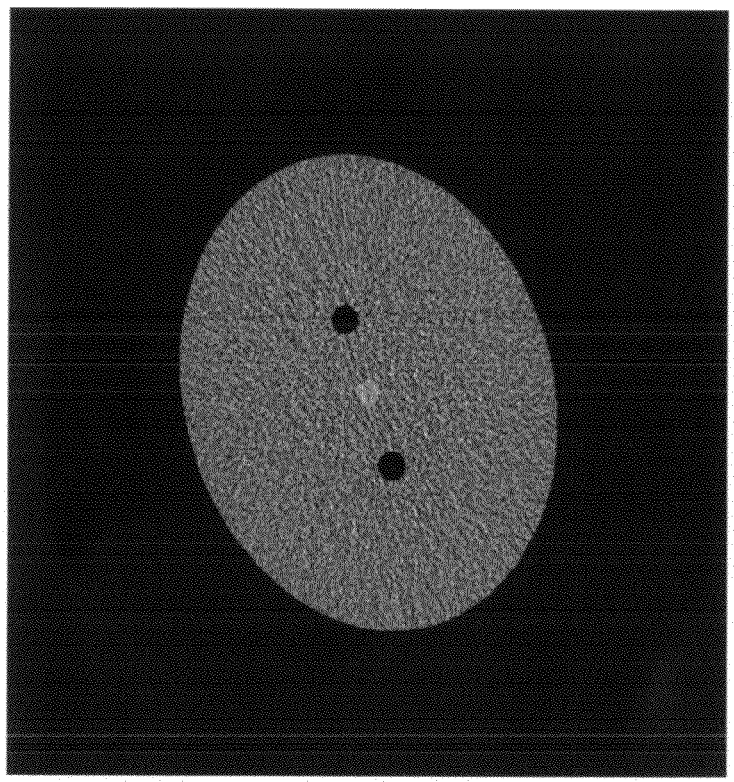
FIG. 8B is a water component image reconstructed from noisy data.
Figure 8A:
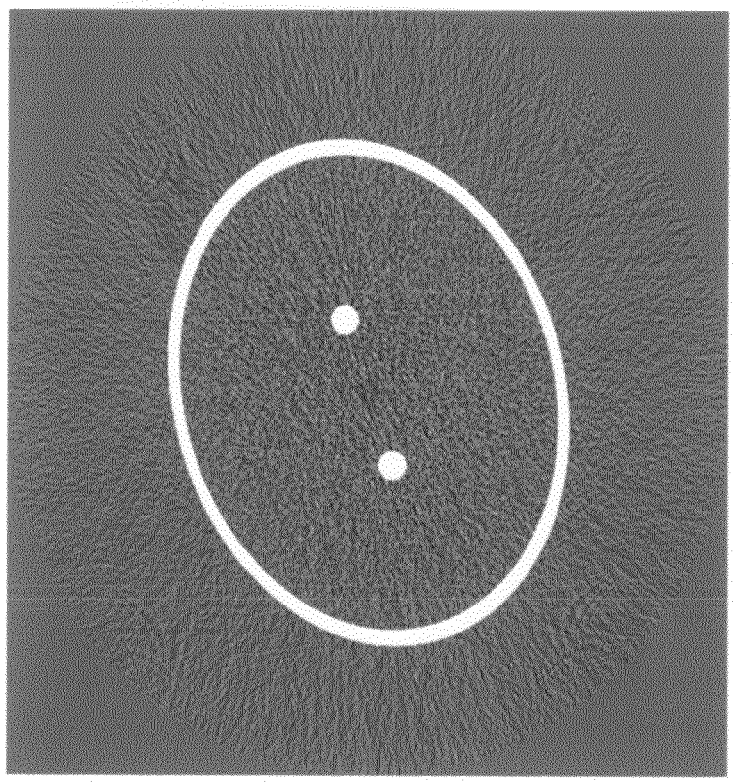
FIG. 8A is a bone component image reconstructed from noisy data.
Figure 8D:
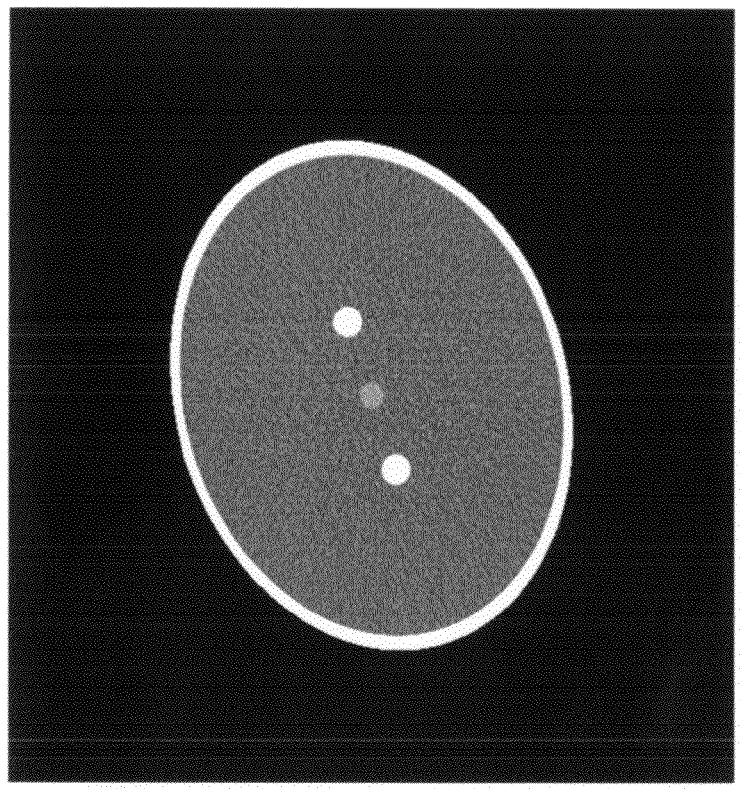
FIG. 8D is a monochromatic image at 80 keV.
Figure 8C:
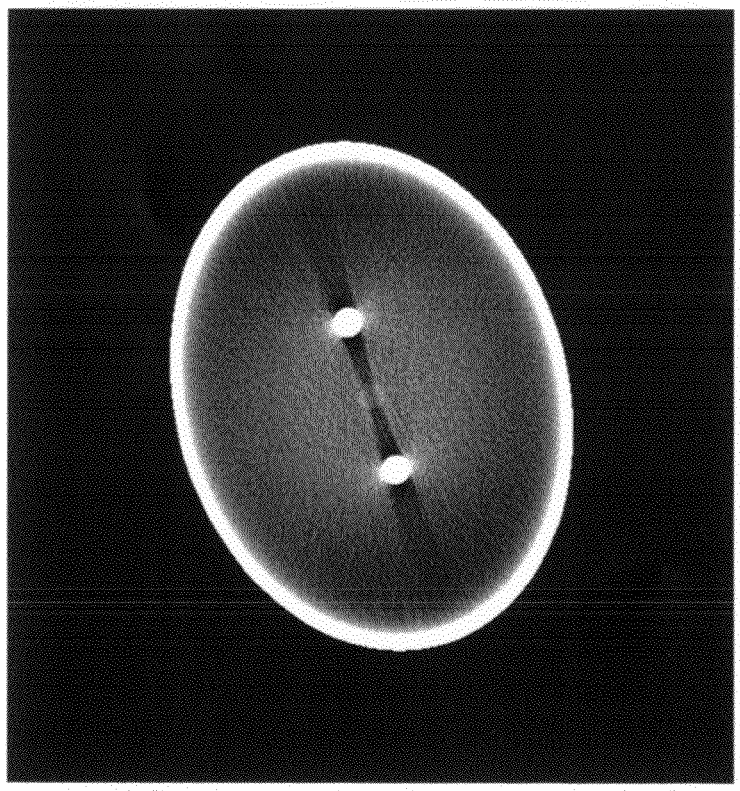
FIG. 8C is a polychromatic projection for 80 kVp.

FIGS. 8A-8D show images reconstructed from noisy data. The Poisson noise model with 10E6 photons for each incident ray is assumed. FIG. 8A shows a bone component image reconstructed from noisy data. FIG. 8B shows a water component image reconstructed from noisy data. FIG. 8C shows a polychromatic image for 80 kVp. FIG. 8D shows a monochromatic image at 80 keV.

The images from dual energy decomposition contain no beam hardening artifacts and the image from poly-chromatic projections shows strong beam hardening artifacts. The reconstructions from noisy data show uniform noise distribution and no significant noise amplification in the monochromatic image at proper energies, e.g. 80 keV.

The dual energy decomposition and calibration methods according to the present invention are stable and may accurately and efficiently produce reconstructed images. A reasonable step thickness of 4 mm for the calibration phantom can generate accurate images although the average attenuation for bone may be underestimated by 10 to 14%.

FIG. 9 shows a graph of energy vs. atomic number. The K-edge energy as a function of atomic number is given by the lower curve 54. The dual energy technique may have problems if tissues have a Z above Z=40. The upper curve 52 separates the graph into a region where Compton dominates (i.e., above curve 52) from the region where Photoelectric dominates (i.e., below curve 52). For example, water with a Z of 7.22, at energies above 26 keV, Compton is more important than Photoelectric but for calcium with a Z of 20, Compton doesn't become more important than Photoelectric until 85 keV.

Although the invention has been described above with respect to dual-energy CT, the invention also applies to multiple-energy CT, and to dual-energy radiography for automatic bone subtractions.

Numerous modifications and variations of the present invention are possible in light of the above teachings. It is therefore to be understood that within the scope of the appended claims, the invention may be practiced otherwise than as specifically described herein.

The invention claimed is:

1. A method of obtaining a computed tomography image of an object, the method comprising:
    obtaining object dual-energy projection data of the object;
    obtaining average attenuation coefficients and non-linear beam hardening coefficients;
    determining, for the object dual-energy projection data, a pair of line integral equations that, upon introducing the average attenuation coefficients, are reorganized into a pair of reorganized line integral equations including linear terms and non-linear beam hardening terms;
    obtaining initial solutions of the reorganized line integral equations by setting the non-linear beam hardening terms to zero;
    iteratively solving the reorganized line integral equations starting with the initial solutions to obtain a first basis line integral solution for a first basis material and a second basis line integral solution for a second basis material; and
    reconstructing the computed tomography image of the object based on the first basis line integral solution for the first basis material and the second basis line integral solution for the second basis material.

2. The method of claim 1, wherein the obtaining object dual-energy projection data of the object further comprises:
    obtaining a first measured amount of energy in a first energy spectrum that passes through a part of the object; and
    obtaining a second measured amount of energy in a second energy spectrum that passes through the part of the object.

3. The method of claim 2, wherein:
    the obtaining the initial solutions further comprises initializing line integrals $L_1(l)$ and $L_2(l)$ along path l as follows $$\begin{pmatrix} L_1 \\ L_2 \end{pmatrix} = D^{-1} \begin{pmatrix} \overline{\mu}_2^L & -\overline{\mu}_2^H \\ -\overline{\mu}_1^L & \overline{\mu}_1^H \end{pmatrix} \begin{pmatrix} g_H \\ g_L \end{pmatrix},$$

where
$D = \overline{\mu}_1^H \overline{\mu}_2^L - \overline{\mu}_1^L \overline{\mu}_2^H$, $g_H$ is object dual-energy projection data of the object measured in a first energy spectrum, $g_L$ is object dual-energy projection data of the object measured in a second energy spectrum, and $\overline{\mu}_{1,2}^{H,L}$ are energy averaged linear attenuation coefficients for the first and second basis materials measured in the first and the second energy spectra, respectively; and the iteratively solving further comprises iteratively solving $$\begin{pmatrix} L_1^n \\ L_s^n \end{pmatrix} = D^{-1} \begin{pmatrix} \overline{\mu}_2^L & -\overline{\mu}_2^H \\ -\overline{\mu}_1^L & \overline{\mu}_1^H \end{pmatrix} \begin{pmatrix} g_H - g_H^{(BH)}(L_1^{n-1}, L_2^{n-1}) \\ g_L - g_L^{(BH)}(L_1^{n-1}, L_2^{n-1}) \end{pmatrix}$$

where E is an energy variable, and n is an integer number of iterations.

4. The method of claim 1, wherein the reconstructing further comprises:
    reconstructing the computed tomography image of the object using Filtered Back-Projection (FBP) or True Cone Beam Tomography (TCOT) reconstruction.

5. The method of claim 1, further comprising:
    obtaining phantom dual-energy projection data of a phantom including the first basis material and the second basis material,
    wherein most of an attenuation by the first basis material in the phantom dual-energy projection data corresponds to a photoelectric attenuation process, and most of an attenuation by the second basis material in the dual-energy projection data corresponds to a Compton attenuation process.

6. The method of claim 5, wherein the obtaining the average attenuation coefficients and the non-linear beam hardening coefficients further comprises:
    obtaining a coefficient of a pure non-linear term of the line integral equation based on the phantom dual-energy projection data; and
    calculating the non-linear beam hardening term based on the obtained coefficient of the pure non-linear term of the line integral equation.

7. The method of claim 5, wherein the average attenuation coefficients include a first average coefficient, a second average coefficient, a third average coefficient, and a fourth average coefficient, and the obtaining the average attenuation coefficients and the non-linear beam hardening coefficients further comprises:
    averaging, to obtain the first average coefficient, a basis attenuation coefficient of the first basis material over a first spectrum of energy used in the obtaining the phantom dual-energy projection data;
    averaging, to obtain the second average coefficient, a basis attenuation coefficient of the first basis material over a second spectrum of energy used in the obtaining the phantom dual-energy projection data;
    averaging, to obtain the third average coefficient, a basis attenuation coefficient of the second basis material over the first spectrum of energy used in the obtaining the phantom dual-energy projection data; and
    averaging, to obtain the fourth average coefficient, a basis attenuation coefficient of the second basis material over the second spectrum of energy used in the obtaining the phantom dual-energy projection data.

8. An apparatus for obtaining a computed tomography image of an object, the apparatus comprising:
    a dual-energy projection data obtaining section configured to obtain object dual-energy projection data of the object;
    a calculating section configured to obtain average attenuation coefficients and non-linear beam hardening coefficients;
    a line integral determining portion configured to determine, for the object dual-energy projection data, a pair of line integral equations that, upon introducing the average attenuation coefficients, are reorganized into a pair of reorganized line integral equations including linear terms and non-linear beam hardening terms;

an initial value obtaining section configured to obtain an initial solution of the reorganized line integral equations by setting the non-linear beam hardening terms to zero;

an iteratively solving section configured to iteratively solve the reorganized line integral equations starting with the initial solutions to obtain a first basis line integral solution for a first basis material and a second basis line integral solution for a second basis material; and a reconstructing section configured to reconstruct the computed tomography image of the object based on the first basis line integral solution for the first basis material and the second basis line integral solution for the second basis material.

9. The apparatus of claim 8, wherein the obtaining object dual-energy projection data of the object further comprises:

a first measured amount obtaining section configured to obtain a first measured amount of energy in a first energy spectrum that passes through a portion of the object; and a second measured amount obtaining section configured to obtain a second measured amount of energy in a second energy spectrum that passes through the portion of the object.

10. The apparatus of claim 9, wherein the average attenuation coefficients include a first average coefficient, a second average coefficient, a third average coefficient, and a fourth average coefficient, and wherein the calculating section further comprises:

a first averaging section configured to obtain the first average coefficient by averaging a basis attenuation coefficient of the first basis material over a first spectrum of energy used in the calibration section to obtain the phantom dual-energy projection data;

a second averaging section configured to obtain the second average coefficient by averaging a basis attenuation coefficient of the first basis material over a second spectrum of energy used in the calibration section to obtain the phantom dual-energy projection data;

a third averaging section configured to obtain the third average coefficient by averaging a basis attenuation coefficient of the second basis material over the first spectrum of energy used in the calibration section to obtain the phantom dual-energy projection data; and a fourth averaging section configured to obtain the fourth average coefficient by averaging a basis attenuation coefficient of the second basis material over the second spectrum of energy used in the calibration section to obtain the phantom dual-energy projection data.

11. The apparatus of claim 9, wherein:

the initial solution obtaining section is further configured to initialize line integrals $L_1(l)$ and $L_2(l)$ along path l as follows $$\begin{pmatrix} L_1 \\ L_2 \end{pmatrix} = D^{-1} \begin{pmatrix} \bar{\mu}_2^L & -\bar{\mu}_2^H \\ -\bar{\mu}_1^L & \bar{\mu}_1^H \end{pmatrix} \begin{pmatrix} g_H \\ g_L \end{pmatrix},$$

where
$D = \bar{\mu}_1^H \bar{\mu}_2^L - \bar{\mu}_1^L \bar{\mu}_2^H$, $g_h$ is object dual-energy projection data of the object measured in a first energy spectrum, $g_L$ is object dual-energy projection data of the object measured in a second energy spectrum, and $\bar{\mu}_{1,2}^{H,L}$ are energy averaged linear attenuation coefficients for the first and second basis materials measured in the first and the second energy spectra, respectively; and the iterative solving section is further configured to iteratively solve $$\begin{pmatrix} L_1^n \\ L_s^n \end{pmatrix} = D^{-1} \begin{pmatrix} \bar{\mu}_2^L & -\bar{\mu}_2^H \\ -\bar{\mu}_1^L & \bar{\mu}_1^H \end{pmatrix} \begin{pmatrix} g_H - g_H^{(BH)}(L_1^{n-1}, L_2^{n-1}) \\ g_L - g_L^{(BH)}(L_1^{n-1}, L_2^{n-1}) \end{pmatrix}$$

where E is an energy variable, and n is an integer number of iterations.

12. The apparatus of claim 8, wherein the reconstructing section is further configured to reconstruct the computed tomography image of the object using Filtered Back-Projection (FBP) or True Cone Beam Tomography (TCOT) reconstruction.

13. The apparatus of claim 8, further comprising:

a calibration section configured to obtain phantom dual-energy projection data of a phantom including the first basis material and the second basis material, wherein most of an attenuation by the first basis material in the phantom dual-energy projection data corresponds to a photoelectric attenuation process, and most of an attenuation by the second basis material in the dual-energy projection data corresponds to a Compton attenuation process.

14. The apparatus of claim 13, wherein the calculating section further comprises:

a coefficient obtaining section configured to obtain a coefficient of a pure non-linear term of the line integral equation based on the phantom dual-energy projection data; and the calculating section is further configured to calculate the beam hardening term based on the coefficient of the pure non-linear term of the line integral equation.

15. A non-transitory computer-readable medium having computer program instructions that, when executed on a computer, cause the computer to perform steps to obtain a computed tomography image of an object, the steps comprising:

obtaining object dual-energy projection data of the object;

obtaining average attenuation coefficients and non-linear beam hardening coefficients;

determining, for the object dual-energy projection data, a pair of line integral equations that, upon introducing the average attenuation coefficients, are reorganized into a pair of reorganized line integral equations including linear terms and non-linear beam hardening terms;

obtaining initial solutions of the reorganized line integral equations by setting the non-linear beam hardening terms to zero;

iteratively solving the reorganized line integral equations starting with the initial solutions to obtain a first basis line integral solution for a first basis material and a second basis line integral solution for a second basis material; and reconstructing the computed tomography image of the object based on the first basis line integral solution for the first basis material and the second basis line integral solution for the second basis material.

* * * * *